United States Patent [19]

Wu et al.

[11] Patent Number: 6,124,496
[45] Date of Patent: Sep. 26, 2000

[54] METHOD OF PREPARING N-(2-AMINOALKYL)-2-AMINOETHOXYLATE ETHANE SULFONATE

[75] Inventors: Jong-Fu Wu; Kun-Lin Cheng, both of Taipei; Wen-Jung Chen, Hsin-Chuang, all of Taiwan

[73] Assignee: China Textile Institute, Taipei Hsien, Taiwan

[21] Appl. No.: 09/173,447

[22] Filed: Oct. 16, 1998

[51] Int. Cl.[7] .................. C07C 309/00; C08G 18/38; C08G 18/70
[52] U.S. Cl. .................. 562/104; 562/107; 528/67; 528/78
[58] Field of Search .................. 562/104, 107; 528/78, 67

[56] References Cited

FOREIGN PATENT DOCUMENTS 54009225  1/1979  Japan .

OTHER PUBLICATIONS

Harrison et al, Amines from Amines, Compendium of Org. Syn. Methods, p. 241, Mar. 1971.

*Primary Examiner*—Paul J. Killos
*Assistant Examiner*—Taylor V Oh
*Attorney, Agent, or Firm*—Rosenberg, Klein & Lee

[57] ABSTRACT

The present invention relates to a synthesis method of thionate diamine by the reaction of alkali metal isethionate with diols to form alkali metal isethionate ethoxylate having the following structural formula:

$$HO(CH_2CH_2O)_nCH_2CH_2SO_3A$$

The above isethionate ethoxylate is then reacted with aliphatic diamine having a Carbon number of 2 to 6 to form a series of N-(2-aminoalkyl)-2-aminoethyoxylate ethane sulfonate having the following structure formula:

$$H_2N-(CH_2)_m-NH-(CH_2CH_2O)_nCH_2CH_2SO_3A$$

wherein m=2–12
  n=1–3
  A=K or Na

3 Claims, No Drawings

METHOD OF PREPARING N-(2-AMINOALKYL)-2-AMINOETHOXYLATE ETHANE SULFONATE

BACKGROUND OF THE INVENTION (a) Field of the Invention

The present invention generally relates to a method of preparing N-(2-aminoalkyl)-2-aminoethyoxylate ethane sulfonate.

(b) Description of the Prior Art

The following citations disclose compounds containing sulfonated diamines:

(bi) Germany patent nos. 2260870, 2551094, 2550797, 2900574, 3630045 and 3836030 disclose the use of sodium salt of N-(2-aminoethyl)-2-aminoethane sulfonic acid as emulsifying agent and chain extender for aqueous PU resins;

(bii) Japan Publication No. 58-59959 discloses sulfonated diamine which can be obtained from the reaction of vinylsulfonic acid sodium salt with aliphatic diamines; and (biii) Germany patent no. 2035729 discloses the production of sulfonated diamines, from the reaction of ethylene diamine and propanesultone and then neutralize with an alkali to form sulfonated diamines, to form an aqueous PU dispersion, wherein its film has excellent water resistant properties.

In order to introduce an ethoxyl group into a sulfonated diamines, an alkali metal isethionate ethoxylate has to be synthesized first. The synthesis methods of these compounds have been taught in U.S. Pat. No. 2,535,678, which discloses the production of alkali metal isethionate ethoxylate by reacting sodium isethionate and triethylene glycol in the present of sodium hydroxide.

U.S. Pat. Nos. 4,091,014 and 4,226,807 disclose a preparation method of ether sulfonate. International Application No. PCT/US95/04178 has also discloses the preparation of alkali metal isethionate ethoxylate.

DETAILED DESCRIPTION OF THE PRESENT INVENTION

The present invention relates to a method of preparing N-(2-aminoalkyl)-2 aminoethyoxylate ethane sulfonate, which is formed from the reaction of alkali metal isethionate ethoxylate having the following structural formula with an aliphatic diamine:

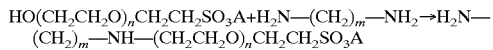

wherein A is potassium or sodium, n is 1–3 and m is 2–12.

In the above reaction, the ideal reacting temperature is ranging from 100 deg C. to 300 deg C., preferably, ranging from 150 to 250 deg C. Any excess of aliphatic diamine is removed by the method of reduced-pressure distillation. During the course of reaction, polar solvents, such as dimethylsulphoxide (DMSO) or dimethylformamide (DMF) may be added. If the polar solvent is not added, the amount of aliphatic diamine has to be in excess.

In accordance with the present invention, N-(2-aminoalkyl)-2-aminoethyoxylate ethane sulfonate may be used to synthesis anionic polyurethane dispersion. To prepare anionic polyurethane dispersion, a polyester or polyether polyol is reacted with a diisocyanate to form a prepolymer. At this instance, an appropriate low boiling point organic solvent such as ketone or methylethylketone, etc. is added, After that, an aqueous solution of N-(2-aminoalkyl)-2-aminoethyoxyyate ethane sulfonate is then added. The amount added is 5 to 200 milliequivalent in 100 g of polymer and an anionic PU dispersion of high molecular weight is thus obtained. The last step of the reaction is the removal of the organic solvent by the method of reduced-pressure distillation. The final product of the reaction is an aqueous PU dispersion with a low volatile organic compound.

The general formula of the above diisocyanate is as follows:

wherein Q is an aliphatic hydrocarbon radical (carbon number is 4 to 12) or cycloaliphatic hydrocarbon radical (carbon number is 6 to 15) or aromatic hydrocarbon radical (carbon number is 6 to 15). These diisocyanates include the following:

tetramethylene diisocyanate, hexamethylene diisocyanate (HDI), 1,4-diisocyanato cyclohexane, 4,4'-diisocyanato dicyclohexylmethane ($H_{12}$MDI), isophorone diisocyanate (IPDI), tetramethylxylylene diisocyanate (TMXDI), diphenylmethane-4,4'-diisocyanate (MDI), toluylene diisocyanate (TDI), xylylene diisocyanate (XDI) and the mixture of the above diisocyanates.

The mole ratio of diisocyanate and polyols (NCO/OH) is ranging from 1.1:1 to 2.5:1. The molecular weight of the ployester polyols is ranging from 400 to 10000, preferably ranging from 400 to 4000. The polyols are obtained via condensation polymerization of diacids with diols in excess. The required diacids includes the following: adipic acid, phthalic acid, tetrahydro phthalic acid, and hexahydro phthalic acid.

The required diols or polyols having molecular weight of 60 to 400, include ethylene glycol, propylene glycol, butane glycol, hexamethylene glycol, glycerol, trimethylol propane, diethylene glycol, triethylene glycol.

The required polyether polyols include polytetramethylene glycol (PTMG), polypropylene glycol (PPG), and polyethylene glycol (PEG). Other types of polyols are polycarbonate polyol, polycaprolactone polyol or the mixtures of the above. The amines chain extender having a molecular weight of 30 to 400, includes ethylene diamine. hexamethylene diamine, isophorone diamine, 2,4-diamino toluene, 4,4'-diamino dicyclohexylmethane, diethylene triamine, triethylene tetramine, hydrazine, and hydrazine hydrate.

EXAMPLE 1

Sodium Salt of N-(2-aminoethyl)-2-aminoethoxylate Sulfonic Acid

In a 2-liter reactor, 300 g (2.02 mole) of isethionic sodium salt, 1510 g (24.3 mole) of ethylene glycol, 7.8 g NaOH and 50 ml of toluene were added. Nitrogen gas was employed to pass through the mixture in the reactor. The reactor was fixed with Dean-Stark. Increased the temperature of the reaction gradually until it reached 190 deg C. At this moment, the water thus formed and toluene were flown down to Dean-Stark via azeotropic distillation. The reaction time was about 8 hour. At low temperature, HCl solution was used to neutralize (at room temperature) until the pH value of the solution was 7 to 8. By the method of reduced-pressure distillation, the remaining ethylene glycol was distilled out at the temperature of 120–140 deg C. At this moment, the product obtained was sodium isethionate ethoxylate, which was a high melting point solid, weighed 382 g and the yield was 98.1%. If diethylene glycol or triethylene glycol was used to replace ethylene glycol, the method of preparation was substantially similar.

300 g (1.56 mole) of the above sodium isethionate ethoxylate and 468 g of ethylene diamine (7.81 moles) were placed in a 1-liter reactor. 3 g of NaOH and 400 ml of dimethyl sulfoxide (DMSO) were added and reacted at the temperature of 200 deg C. for 6 hour. Decreased the temperature of the reaction, and then neutralized with dilute HCl until the pH value was at 7–8. The excess ethylene glycol and solvent, DMSO, were removed via the method of reduced-pressure distillation. The product thus obtained was 319 g of a high melting point of sodium salt of N-(2-aminoethyl)-2-aminoethoxylate sulfonic acid, yield: 87.03%.

EXAMPLE 2

In a 1-liter reactor, 320 g of polybutylene adipate (PBA) (OH value=56) was poured into the reactor. The polyester is dehydrated in vacuum at 120 deg C. for 30 minutes and then decreased the temperature to 90 deg C. 23.3 g of hexamethylene diisocyanate(HDI) and 15.4 g of isophorone diisocyanate (IPDI) were added and reacted for 3 hours. Added with 200 ml acetone and lowered the temperature to 50 deg C. When the temperature was at 50 deg C., added 16.04 g of sodium salt of N-(2-aminoethyl)-2-aminoethoxylate sulfonic acid (45% in water) in and 0.8 g hydrazine hydrate and continued the reaction for 15 minutes and then added with 370 g of deioned water to proceed with dispersion and reduced pressure distillation to remove the acetone at 50 deg C. A solid content of 50% aqueous PU dispersion was obtained, having a particle size of 450 nm, $SO_3Na$ content being 17.4 meq/100 g polymer.

While the invention has been described in conjunction with specific embodiments thereof, it is evident that many alternatives, modifications, and variations will be apparent to those skilled in the art in light of the foregoing description. Accordingly, it is intended to embrace all such alternatives. modifications, and variations as fall within the spirit and broad scope of the appended claims.

What is claimed is:

1. A method of preparing N-(2-aminoalkyl)-2 aminoethoxylate ethane sulfonate comprising the step of reacting an alkali metal isethionate ethoxylate with an aliphatic diamine at a temperature within a range of 100 to 300 degrees C. to form a product having the following structural formula:

wherein m=2–12, n=1–3 and A=K or Na.

2. The method as set forth in claim 1, wherein the step of reacting includes the step of adding an organic polar solvent.

3. A method of preparing an aqueous polyurethane dispersion, comprising the steps of:

(a) reacting an alkali metal isethionate ethoxylate with an aliphatic diamine at a temperature within a range of 100 to 300 degrees C. to form a product having the following structural formula:

wherein m=2–12, n=1–3 and A=K or Na;

(b) reacting a polymer selected from the group consisting of polyester and polyether polyol with a diisocyanate to form a prepolymer;

(c) adding a low boiling point organic solvent to the prepolymer of step (b);

(d) forming an aqueous solution of the product of step (a);

(e) adding the aqueous solution of step (d) to the organic solvent and prepolymer of step (c); and, (f) removing the organic solvent.

* * * * *